United States Patent
Stamm et al.

(10) Patent No.: US 7,301,048 B2
(45) Date of Patent: Nov. 27, 2007

(54) PROCESS FOR ISOLATING VINYL ACETATE

(75) Inventors: Johann Stamm, Frankfurt (DE); Bernd Rinne, Frankfurt (DE); Stefan Hess, Gross-Gerau (DE); Hans-Jochen Sachs, Frankfurt (DE); Michael Sehr, Limburg (DE); Michael J. Bayer, Eschborn (DE); Berthold Nuber, Frankfurt (DE); Martin Wagner, Frankfurt (DE)

(73) Assignee: Celanese Chemicals Europe GmbH, Oberhausen (DE)

( * ) Notice: Subject to any disclaimer, the term of this patent is extended or adjusted under 35 U.S.C. 154(b) by 0 days.

(21) Appl. No.: 11/484,419

(22) Filed: Jul. 11, 2006

(65) Prior Publication Data

US 2007/0032678 A1    Feb. 8, 2007

(30) Foreign Application Priority Data

Aug. 5, 2005    (DE)    ............... 10 2005 036 930

(51) Int. Cl.
*C07C 67/48*    (2006.01)

(52) U.S. Cl. .............. 560/248; 560/261; 560/263

(58) Field of Classification Search ................ 560/243, 560/248, 261, 263
See application file for complete search history.

(56) References Cited

U.S. PATENT DOCUMENTS

| 3,591,463 | A | | 7/1971 | Copelin |
| 4,818,347 | A | * | 4/1989 | Roscher et al. ............... 203/42 |

FOREIGN PATENT DOCUMENTS

| DE | 1 278 430 | 2/1967 |
| DE | 2610624 C2 | 9/1977 |
| DE | 100 42 695 A1 | 8/2000 |
| EP | 0 423 658 A2 | 4/1991 |

* cited by examiner

*Primary Examiner*—Yvonne Eyler
*Assistant Examiner*—Sudhakar Katakam
(74) *Attorney, Agent, or Firm*—Charles A. Muserlian

(57) ABSTRACT

A process for isolating vinyl acetate from the gas mixture formed in the reaction of ethylene with acetic acid and oxygen in the gas phase over catalysts comprising palladium or palladium compounds, with recirculation of the acetic-acid solution obtained in the circulating gas scrubber to the first distillation column (predewatering column).

15 Claims, 1 Drawing Sheet

PROCESS FOR ISOLATING VINYL ACETATE

The present invention relates to a process for isolating vinyl acetate from the gas mixture formed in the reaction of ethylene with acetic acid and oxygen in the gas phase over catalysts comprising palladium or palladium compounds, with recirculation of the acetic-acid solution obtained in the circulating gas scrubber to the first distillation column.

The preparation of vinyl acetate by reaction of ethylene with acetic acid and oxygen or oxygen-containing gases in the gas phase over fixed-bed catalysts is already known. The reaction is generally carried out at pressures of from 1 to 2.5 MPa and temperatures of from 100 to 250° C. Suitable catalysts comprise a noble metal component and an activator component. The noble metal component comprises palladium and/or compounds thereof; in addition, gold or its compounds can also be present. The activator component comprises compounds of elements of the $1^{st}$ main group and/or the $2^{nd}$ main group and/or cadmium. These active components are applied to supports in finely divided form, with silica or aluminum oxide generally being used as support material.

In general, the palladium content of the catalyst is from 0.5 to 5% by weight.

If gold or one of its compounds is used, it is added in a proportion of from 0.01 to 4% by weight.

Each individual activator is likewise generally added in a proportion of from 0.01 to 4% by weight. In the case of all three percentages indicated, the metal part of the component is in each case based on the total mass of the supported catalyst. Preference is given to the following catalysts: palladium/alkali element/cadmium and palladium/gold/alkali element, with palladium and gold being able to be present as metals or compounds in the finished catalyst and potassium being preferred as alkali element. Potassium is used in the form of a carboxylate, in particular as acetate.

Particular preference is given to the catalysts palladium acetate/potassium acetate/cadmium acetate and palladium acetate/barium acetoaurate/potassium acetate.

In the multistage catalytic process, vinyl acetate and water are formed in equimolar amounts, as shown in the following overall equation:

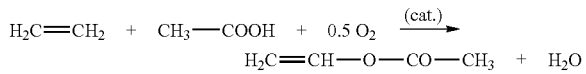

The total oxidation of ethylene, which cannot be entirely avoided, forms $CO_2$ and water:

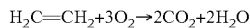

More than 1 mol of water is thus obtained per mole of vinyl acetate; in general, the weight of water is about one quarter of the weight of the vinyl acetate formed.

Apart from $CO_2$, small amounts of other by-products, including ethyl acetate, are formed in a proportion of about 1000-2000 ppm by weight, based on the vinyl acetate formed.

Only a small amount of not more than 250 ppm by weight of ethyl acetate is permitted in the pure vinyl acetate. The removal of vinyl acetate requires a large amount of energy and the prior art addresses various methods of reducing the energy consumption in the purification of vinyl acetate with removal of ethyl acetate and other by-products.

The mixture used for the reaction contains a multiple of the stoichiometrically required amount of ethylene. Accordingly, the ethylene conversion is relatively low (about 10%) and the unreacted ethylene has to be recirculated to the reaction zone. Vinyl acetate is usually separated off from the mixture of gaseous reaction products in a multistage process.

In the process described in DE-A1-3 422 575, the hot gas mixture leaving the vinyl acetate reactor, which consists essentially of ethylene, acetic acid, vinyl acetate, water, carbon dioxide, oxygen and inerts such as, for example, nitrogen and argon and contains ethyl acetate is introduced into a first distillation column which operates without additional heating, known as the predewatering column. The gas mixture leaving the top of this column is firstly brought into contact with the runback to the predewatering column in a heat exchanger, resulting in the gas mixture being cooled and the runback being correspondingly heated. The gas mixture subsequently goes from the heat exchanger to a condenser. The material which is liquefied here is collected in a collection vessel where separation into an aqueous phase and an organic phase occurs. The aqueous phase is discharged while all or part of the organic phase is recirculated as runback to the top of the predewatering column.

The material which has not been liquefied in the condenser comprises still gaseous vinyl acetate. This is scrubbed out of the gas mixture in a scrubbing column operated using acetic acid as scrubbing liquid, known as the circulating gas scrubber. The remaining tailgas is recirculated to the reactor. The outflow from the bottom of the circulating gas scrubber and the remainder of the liquefied organic phase from the condensate of the predewatering column is collected in a further vessel if not all of the liquefied organic phase from the condensate is used as runback to the predewatering column.

A mixture comprising vinyl acetate, acetic acid and about half of the water of reaction and also by-products is obtained at the bottom of the predewatering column. The other half of the water of reaction has already been separated off without introduction of energy and forms the aqueous phase of the condensate formed on cooling of the vapor from the top of the predewatering column.

The bottom product from the predewatering column is firstly fed into a collection vessel, also referred to as the crude vinyl acetate collection vessel, and subsequently worked up in a second distillation column, known as the azeotrope column. Vinyl acetate saturated with water is obtained as overhead product, and a side stream comprising ethyl acetate and a bottom product which is recirculated to the system as recycle acetic acid are obtained. The side stream comprising ethyl acetate is discharged. The vinyl acetate saturated with water which is not returned as runback to the top of the second distillation column is combined with the outflow from the bottom of the circulating gas scrubber and the remainder of the liquefied organic phase from the condensate from the predewatering column.

The mixture is subsequently fed to a further, third distillation column, known as the dewatering column. The vapor from the top of this column is, after condensation, virtually entirely recirculated as runback. The side offtake stream is separated into an aqueous phase and an organic phase, with the aqueous phase then being discharged and the organic phase being returned to the column. A dry vinyl acetate/acetic acid mixture is taken off at the bottom of the dewatering column and fed to a further, fourth column, known as the pure vinyl acetate column. In this column, vinyl acetate which is virtually free of ethyl acetate is obtained as overhead product, while the bottoms from this column, which comprise acetic acid, high boilers and traces of vinyl acetate and ethyl acetate, are, after discharge of a substream, recirculated to the process.

A further variant of the known process for working up vinyl acetate is known from EP-A2-0 423 658. In this variant, the bottom product from the circulating gas scrubber is not combined directly with the water-containing vinyl acetate obtained in the azeotrope column but is firstly introduced into a further column in which a vinyl acetate/water azeotrope is obtained as overhead product and acetic acid, which is recirculated to the process, is obtained as bottom product. Aqueous vinyl acetate obtained in this additional column is combined with the vinyl acetate saturated with water obtained from the azeotrope column and is worked up by a method corresponding to the process of DE-A1-3 422 575 in the downstream dewatering column and pure vinyl acetate column. The process of EP-A2-0 423 658 requires about the same distillation energy for separating off ethyl acetate as does the process of DE-A1-3 422 575, but requires a smaller amount of plates in the column, which incurs lower capital costs. The uncondensed part of the vinyl acetate from the predewatering column, which is scrubbed out by means of acetic acid in the circulating gas scrubber and is obtained as acetic-acid solution, and the organic phase of the condensate from the predewatering column contain virtually no ethyl acetate and an energy-intensive removal of ethyl acetate from these vinyl acetate streams becomes unnecessary. However, this process variant requires operation of an additional distillation column for fractionating the outflow from the bottom of the circulating gas scrubber.

The known work-up processes for recovering pure vinyl acetate still have some disadvantages. Thus, the outflow from the bottom of the circulating gas scrubber and the outflow from the bottom of the predewatering column contain considerable amounts of gases, especially ethylene, in dissolved form. The depressurization of the outflow from the bottom of the predewatering column and from the circulating gas scrubber in the crude vinyl acetate collection vessel therefore liberates an appreciable amount of recycle gas which has to be compressed in a recycle gas compressor with a high consumption of energy before it can be returned to the reaction circuit. In general, the crude vinyl acetate is depressurized from a pressure in the range from 0.5 to 2.0 MPa to a pressure in the range from 0.02 to 0.2 MPa. The gas formed in the depressurization comprises predominantly ethylene and also carbon dioxide, nitrogen and further inerts such as argon and also organic constituents such as acetic acid and small amounts of vinyl acetate and ethyl acetate. This gas is also referred to as recycle gas which is recirculated to the process.

A characteristic of the known work-up process is the combination of the acetic-acid solution obtained from the outflow from the bottom of the circulating gas scrubber with the vinyl acetate saturated with water from the overhead product of the azeotrope column and the remainder of the liquefied organic phase from the condensate from the predewatering column. For this reason, an acetic-acid mixture, from which acetic acid has to be separated off with a high consumption of energy, is passed to the further purification stages occurring in the downstream dewatering column and pure vinyl acetate column. In addition, the dewatering column and the pure vinyl acetate column have to be constructed using corrosion-resistant materials which are not sensitive to acetic acid.

Likewise, the condensate from the predewatering column which is not returned as runback to the top of the predewatering column still contains a certain amount of ethyl acetate. Since this stream is combined only after the azeotrope column with the vinyl acetate saturated with water obtained as overhead product there, the downstream dewatering column and pure vinyl acetate column are supplied with a stream which contains ethyl acetate and from which ethyl acetate can be separated off only with high consumption of energy.

Finally, improved removal of water and ethyl acetate in a step which is as early as possible in the work-up process is desirable to reduce the amount of these undesirable materials carried through the overall work-up process as much as possible and to avoid the associated, energy-intensive removal in the pure vinyl acetate distillation.

The invention accordingly provides a process for separating off vinyl acetate from the gas mixture formed in the reaction of ethylene with acetic acid and oxygen in the gas phase over catalysts comprising palladium or palladium compounds, which comprises a) introducing the gas mixture leaving the reaction zone into a first distillation column, b) cooling the gas mixture leaving the top of the first distillation column to from −20 to +50° C., with the condensate obtained separating into a water phase and an organic phase, c) taking off the water phase formed in step b), d) recirculating all or part of the organic phase formed in step b) as runback to the top of the first distillation column utilized in step a) and taking off part of the organic phase which is not used as runback, e) scrubbing the gas comprising vinyl acetate which is not condensed in step b) in a scrubbing column by means of at least 90% strength aqueous acetic acid and obtaining an acetic-acid solution comprising vinyl acetate at the bottom, f) feeding the bottom product comprising vinyl acetate, ethyl acetate, acetic acid and water from step a) into a collection vessel and depressurizing the pressurized liquid so as to form a gas, g) feeding the liquid obtained in the depressurization in step f) into a second distillation column and taking off a side stream comprising ethyl acetate from an enrichment zone above its bottom, h) utilizing all or part of the bottom product comprising acetic acid and water from step g) for the gas scrub in step e), i) cooling the overhead vapor from step g), with the condensate obtained separating into an aqueous phase and an organic phase, j) taking off the aqueous phase formed in step i), k) recirculating part of the organic phase formed in step i) as runback to the top of the second distillation column utilized in step g) and taking off the remainder, wherein l) part of the bottom product from the scrubbing column utilized in step e) is firstly cooled with pumped circulation and recirculated to the bottom of the scrubbing column utilized in step e), the remainder is taken off and the part taken off is heated to a temperature of at least 30° C. and fed into the lower part of the first distillation column utilized in step a), m) the remaining organic phase taken off in step d) is depressurized, the gas formed in the depressurization is combined with the gas formed in step f) and the combined gas is returned to the process, n) the organic phase obtained in step m) is combined with the organic phase obtained in step i) and the remaining part of the organic phase taken off in step k) which has not been used as runback is introduced into a third distillation column, o) the overhead product from the third distillation column in step n) is cooled and the low boilers obtained and the water obtained are separated off, p) the bottom product from the third distillation column in step n) is introduced into a fourth distillation column, q) pure vinyl acetate is taken off at the top of the fourth distillation column used in step p).

In step a), the gas mixture leaving the reaction zone is preferably firstly cooled to from 115° C.-150° C. by means of the colder circulating gas in the countercurrent heat exchanger which is thus heated and then recirculated to the reaction. In this step, no condensation of the liquefiable components occurs and the gas mixture is introduced into the first distillation column, also known as predewatering column.

The amount of organic phase formed in step b) is dependent on the temperature to which cooling is carried out in this step. That part of the organic phase from step b) which is not utilized as runback for step d) is taken off and depressurized from a pressure of from 0.5 to 2.0 MPa to a pressure of from 0.02 to 0.2 MPa, preferably to from 0.1 to 0.15 MPa, in step m). The liquid obtained is combined in step n) with the organic phase from the condensed overhead product from the second distillation column, also referred to as azeotrope column (step i). The two organic phases are preferably combined in the phase separator of the azeotrope column. The proportion of the organic phase which is not returned as runback to the top of the azeotrope column in step n) is introduced into a third distillation column, also referred to as dewatering column.

The cooling temperature in step b) and the proportion of the organic phase formed in b) which is utilized as runback in step d) are preferably selected so that very little vinyl acetate but preferably all of the ethyl acetate are present in the bottom product of step a).

A characteristic of the mode of operation according to the invention is the operation of the scrubbing column used in step e) and the recirculation of the outflow from the bottom of the scrubbing column to the lower part of the first distillation column used in step a). Part of the bottoms from the scrubbing column, also referred to as circulating gas scrubber, is circulated by pumping, with the part of the bottom product from the scrubbing column which is conveyed around the pumped circuit being cooled. Cooling of the bottom product is carried out using means with which those skilled in the art are familiar, for example heat exchangers. The part of the bottom product which is not conveyed around the pumped circuit is taken off from the scrubbing column, heated to a temperature of at least 30° C., preferably from 60° C. to 120° C., in particular from 60° C. to 100° C., and fed into the lower part of the first distillation column used in step a). To effect heating, the bottom product pumped off from the scrubbing column is advantageously passed through a heat exchanger.

The heated bottoms from step l) are preferably fed into the first distillation column at the $2^{nd}$ to $15^{th}$ plate, in particular the $5^{th}$ to $10^{th}$ plate, calculated from the bottom of the column.

As a result of the recirculation of the heated bottom product from the scrubbing column in step e) to the lower part of the first distillation column used in step a), the temperature of the outflow from the bottom of the scrubbing column, whose temperature without this measure is generally from 30 to 50° C., is significantly increased. Here, in a first step, the bottoms are firstly heated, for example in a heat exchanger, to a temperature of at least 30° C., preferably from 60° C. to 120° C. and in particular from 60° C. to 100° C. When the resulting heated bottoms from the circulating gas scrubber are fed into the lower part of the first distillation column, this stream is heated again, generally to a temperature of from 80° C. to 150° C., which also corresponds to the temperature of the bottoms from the first distillation column. This heating of the bottoms from the scrubbing column reduces the solubility of the gaseous components in the acetic-acid, crude vinyl acetate. The gaseous components, in particular ethylene and carbon dioxide, are driven off to a greater extent via the top of the first distillation column and are returned to the gas circuit at a very early point of the work-up process. The depressurization of the crude product therefore results in formation of less gas. The depressurization is carried out in a collection vessel, also referred to as crude vinyl acetate collection vessel, from a pressure of from 0.5 to 2.0 MPa to a pressure of from 0.02 to 0.2 MPa, preferably to from 0.1 to 0.15 MPa. The gas obtained in the depressurization is also referred to as recycle gas and comprises predominantly ethylene and additionally carbon dioxide and further inerts such as nitrogen and argon and also organic constituents such as acetic acid and small amounts of vinyl acetate and ethyl acetate. A smaller amount of energy is therefore required in the recirculation of the recycle gas to the process in order to compress the recycle gas to the pressure of the reactor again. Some of the load is therefore taken off the recycle gas compressor by the recirculation according to the invention of the bottoms from the scrubbing column in step e), which brings a significant energy saving.

Furthermore, the introduction of the acetic-acid solution from the scrubbing column into the lower part of the first distillation column, preferably at the $2^{nd}$ to $15^{th}$ plate, in particular the $5^{th}$ to $10^{th}$ plate, calculated from the bottom of the column, achieves a scrubbing effect. Ethyl acetate is scrubbed into the bottom of the first distillation column and discharged via the bottom.

Vinyl acetate is present in the bottom product from the first distillation column, in the acetic-acid scrubbing solution which is formed in step e) and is recirculated in step l) to the lower part of the first distillation column and in the part of the organic phase formed in step b) which is not utilized as runback in step d). The vinyl acetate content of these three streams depends on the mode of operation of the plant and is not critical for carrying out the process of the invention.

The overhead product from the first distillation column contains only very small amounts of ethyl acetate, and the runback recirculated in step d) and the part of the organic phase which is not used as runback are low in ethyl acetate and can be processed further without further measures which require removal of ethyl acetate. For this purpose, the organic phase which is taken off is depressurized in step m) and the liquid obtained is combined with the organic phase obtained in step i), which is obtained from the overhead product from the second distillation column, also referred to as azeotrope column. Part of the combined organic phases is recirculated as runback to the top of the azeotrope column. The remainder is fed to the third distillation column, also referred to as dewatering column (step n).

The gas obtained in the depressurization in step m) is also referred to as recycle gas and has approximately the same composition as the recycle gas obtained in step f). Both recycle gas streams are combined, then compressed in a recycle gas compressor and subsequently recirculated to the process. The purified recycle gas is advantageously combined with the tailgas obtained in the acetic acid scrub in step e), which is also referred to as circulating gas. The combined gas streams are compressed and, after discharge of a proportion containing inerts, recirculated to the vinyl acetate reactor again.

At least part of the bottom product from the second distillation column (step g)) is used in the gas scrub of step e). The bottom product comprises mainly acetic acid and contains not more than 10% by weight of water. Part of the bottom product which is not required in step e) is preferably recirculated to the reactor as recycle acetic acid after a small part has been discharged to remove high boilers and polymers.

In step n), the amount of the combined organic phase from steps i) and m) which is recirculated as runback is preferably only the amount required for the overhead vapor from the second distillation column to contain very little ethyl acetate. That part of the organic phase which is not required for this purpose is introduced into the third distillation column, also referred to as dewatering column.

In step o), the condensed overhead product from the third distillation column is not all utilized as runback but a part which is sufficient to separate off low boilers and water is taken off.

In step p), the bottoms from the third distillation column, which consist essentially of dry vinyl acetate, are fed into a fourth distillation column, known as the pure vinyl acetate column, from which pure vinyl acetate is taken off as overhead product (step q).

The first, second, third and fourth distillation columns utilized in the claimed work-up process for vinyl acetate are operated at temperatures, pressures and reflux ratios appropriate for the utilization of the capacity of the plant.

BRIEF DESCRIPTION OF DRAWING

The process of the invention is illustrated by means of FIG. 1. Measures known per se, e.g. addition of stabilizer, are not shown.

The recirculated gas mixture comprising ethylene, oxygen and $CO_2$ and also inerts and small amounts of organic components such as acetic acid, also referred to as circulating gas, is introduced via line (1) into an acetic acid vaporizer (2) configured as a tray column in which the gas stream is laden with acetic acid which is fed in via line (3). The gas mixture leaving the acetic acid vaporizer (2) is fed via a steam-heated line (4) to the vinyl acetate reactor (5).

Figure 1:
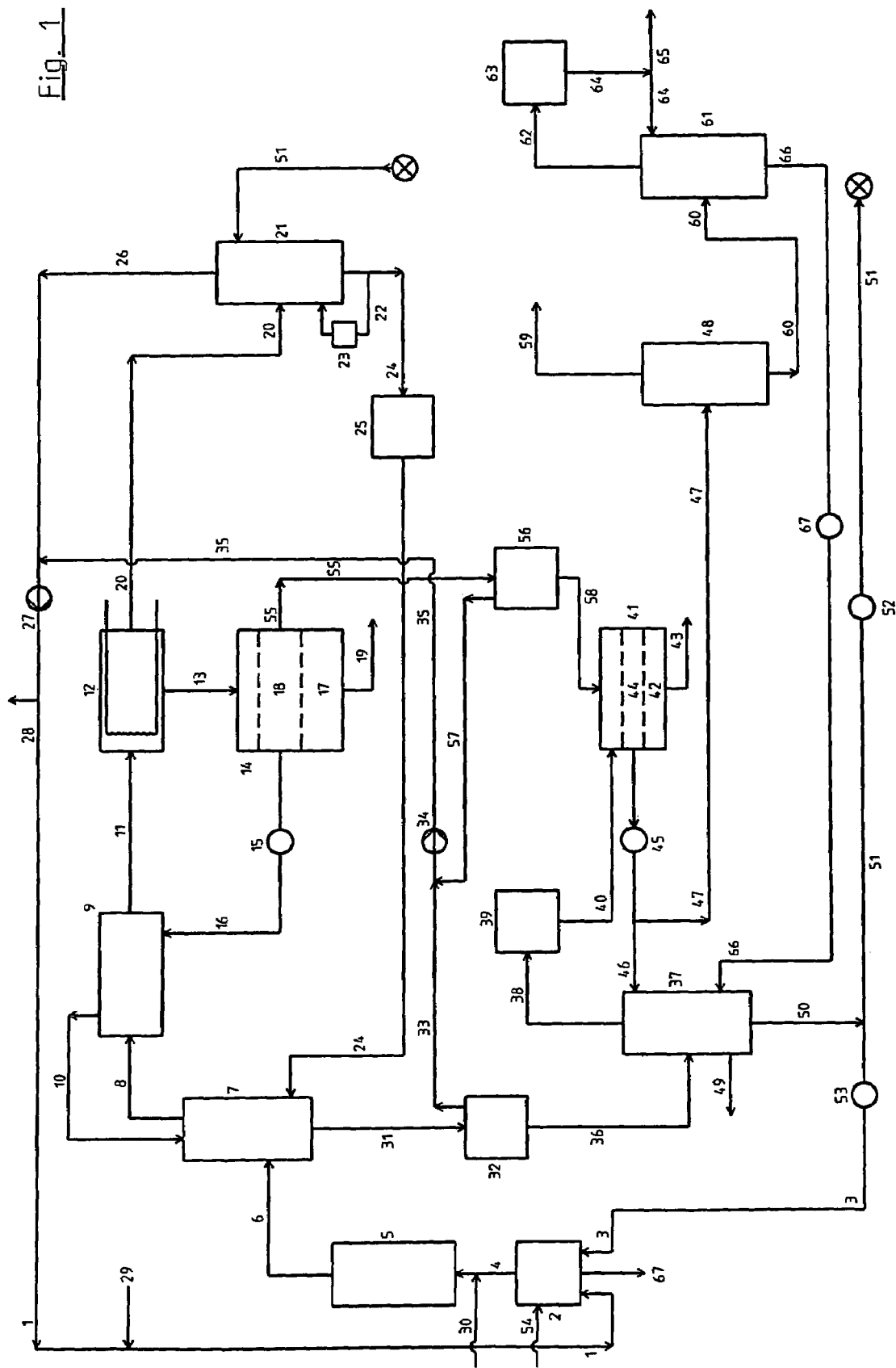

The gas mixture leaving the vinyl acetate reactor (5), which consists essentially of ethylene, acetic acid, vinyl acetate, water, carbon dioxide, oxygen and inert gases such as nitrogen and argon, is introduced via line (6) into the first distillation column, the predewatering column (7). The predewatering column (7) has a design known per se.

The gas mixture leaving the top of the predewatering column (7) goes via line (8) to a heat exchanger (9) where it is subjected to countercurrent heat exchange with the runback which enters via line (16) and is returned via line (10) to the predewatering column (7). The gas mixture goes from the heat exchanger (9) via line (11) to a water-cooled condenser (12) in which it is cooled to about 35° C. The material liquefied here goes via line (13) to the vessel (14) where it is collected. The proportion of liquid exceeding a particular level in the collection vessel (14) is pumped by means of the pump (15) via line (16), the heat exchanger (9) and line (10) back into the predewatering column (7). After some time, the condensate obtained in the collection vessel (14) separates into two phases (17) and (18), of which the aqueous phase (17) is discharged via line (19) and only the organic phase (18) is pumped back either in its entirety or partly via line (16), the heat exchanger (9) and line (10) as runback to the top of the predewatering column (7).

The gas mixture leaving the condenser (12) via line (20) is scrubbed and freed of uncondensed vinyl acetate in the scrubbing column (21) (circulating gas scrubber) by means of the acetic acid introduced via line (51). The bottoms from the circulating gas scrubber (21) are separated, with a substream being circulated by pumping via line (22) and recirculated with cooling by means of the heat exchanger (23) to the lower part of the circulating gas scrubber (21) and the other part of the bottoms being conveyed via line (24) through a heat exchanger (25) in which the bottoms are heated to a temperature of at least 30° C., preferably from 60 to 120° C. and in particular from 60 to 100° C. The bottom product which has been heated in this way is subsequently pumped back to the lower part of the predewatering column (7), preferably at the $2^{nd}$ to $15^{th}$ plate, in particular the $5^{th}$ to $10^{th}$ plate, calculated from the bottom of the column.

The tailgas or circulating gas (ethylene, unreacted oxygen and $CO_2$ formed as by-product) leaving the scrubbing column (21) via line (26) is combined with the recycle gas comprising predominantly ethylene and additionally $CO_2$, inerts such as nitrogen and argon and also acetic acid and small amounts of vinyl acetate and ethyl acetate which is brought via line (35), compressed by means of the circulating gas compressor (27) and recirculated via line (1) and the acetic acid vaporizer (2) to the reactor (5). Part of the circulating gas is removed as offgas via line (28) to discharge inert constituents. Fresh ethylene is introduced via line (29) and fresh oxygen is introduced via line (30).

The liquid obtained at the bottom of the predewatering column (7), which comprises mainly vinyl acetate, acetic acid and water and contains virtually all the ethyl acetate, is fed via line (31) to a vessel (32), also referred to as crude vinyl acetate collection vessel, and depressurized there, preferably to a pressure of from 0.02 to 0.2 MPa, in particular to a pressure of from 0.1 to 0.15 MPa. The recycle gas formed here, which comprises predominantly ethylene and additionally $CO_2$, inerts such as nitrogen and argon and also organic constituents such as acetic acid is discharged via line (33), combined with the recycled gas brought via line (57), which has approximately the same composition, and, after compression in the recycle gas compressor (34), combined via line (35) with the circulating gas from the circulating gas scrubber (21) brought via line (26). The organic phase obtained after depressurization in the crude vinyl acetate collection vessel (32) is taken off via the line (36) and introduced into the second distillation column (37), also referred to as azeotrope column.

The vapor from the top of the second distillation column (37) is conveyed via line (38) to the condenser (39) and condensed there. The condensate fed via line (40) to the phase separator (41) separates into an aqueous phase (42) which is taken off via line (43) and an organic phase (44) which is combined with the organic phase brought via line (58). The organic phase combined in the phase separator (41) is discharged by means of the pump (45). Part of the organic phase discharged is fed via line (46) to the top of the azeotrope column (37) and serves as runback there. The part which is not used as runback is discharged via line (47) and fed to a third distillation column (48), viz. the dewatering column. The ethyl acetate introduced via line (36) into column (37) is taken off from an enrichment zone above the bottom of the column (37) via line (49). The bottom product from the column (37) comprises virtually all the acetic acid obtained in the vinyl acetate work-up, not more than 10% by weight of water and also small amounts of high boilers and polymers and only traces of vinyl acetate and ethyl acetate.

The aqueous acetic acid is taken off from the bottom of the column (37) via the line (50) and divided. Depending on the design of the scrubbing column (21) and the temperature of the gas to be scrubbed, differing amounts of acetic acid are required as scrubbing liquid. The proportion required for the acetic acid scrub in step e) is fed via line (51) and the pump (52) to the scrubbing column (21). The remainder is fed via the pump (53) and line (3) to the acetic acid vaporizer (2). Fresh acetic acid is fed in an amount corresponding to the amount of acetic acid consumed in the reaction to the top of the acetic acid vaporizer (2) via line (54) and simultaneously serves as scrubbing solution for the recovered acetic acid brought via line (3), also referred to as recycle acetic acid.

The remainder of the organic phase (18) from the collection vessel (14) is, if not all of the organic phase (18) is used as runback in the predewatering column (7), fed via line (55) to the depressurization vessel (56). The recycle gas formed during the depressurization to a pressure of from 0.02 to 0.2 MPa, preferably from 0.1 to 0.15 MPa, is discharged via line (57), combined with the recycle gas brought via line (33) and, after compression by means of the recycle gas compressor (34), recirculated to the process via line (35).

The liquid obtained in the vessel (56) is fed via line (58) to the phase separator (41) from where the combined organic phases are partly fed as runback via line (46) to the azeotrope column (37) and partly as feed via line (47) to the third distillation column (48), also referred to as dewatering column. The feed to the dewatering column is virtually free of acetic acid.

The low boilers and last residues of water present in the vapor from the top of the column (48) are conveyed away via the line (59) and discharged from the work-up process.

The virtually water-free vinyl acetate obtained at the bottom of the column (48) is fed via line (60) to the fourth distillation column (61), also referred to as pure vinyl acetate column. The vapor from the top of this column goes via line (62) to the condenser (63). The condensate obtained is pure vinyl acetate which is free of ethyl acetate. A very small part of this vinyl acetate is recirculated as runback to the column (61) via line (64). Pure vinyl acetate is taken off via line (65). The bottom product from the column (61), which contains small amounts of ethyl acetate, polymers and high boilers, is recirculated via line (66) and the pump (67) to the column (37). From the acetic acid vaporizer (2), to which all high boilers and polymers are finally recirculated, a substream is taken off via line (67) to discharge polymers.

The measure important to the work-up process of the invention is the recirculation of the heated, acetic-acid bottoms from the scrubbing column (21) to the lower part of the predewatering column (7), with the previously heated, acetic-acid bottoms from the scrubbing column being heated once more. This measure is surprisingly associated with a variety of advantages.

This measure results in a reduction in the solubility of the gaseous components, in particular ethylene and carbon dioxide, which are present in the outflow from the bottom of the circulating gas scrubber and are driven off via the top of the first distillation column and are returned to the circulating gas at an early stage of the process.

As a result, less recycle gas is obtained in the depressurization and this is compressed with lower energy consumption in the recycle gas compressor (34) and returned to the process. The load on the recycle gas compressor is thus reduced.

The introduction of the heated, acetic-acid bottoms from the scrubbing column (21) into the lower part of the predewatering column (7) achieves a scrubbing effect and virtually all of the ethyl acetate is scrubbed into the bottom of the predewatering column (7) and discharged via the bottoms. Only a very small amount of ethyl acetate is carried into the organic phase (18) which collects in the collection vessel (14). The stream taken off via line (55) therefore contains hardly any ethyl acetate. A larger amount of this can therefore be allowed compared to the known mode of operation, as a result of which the loading of the azeotrope column (37) is reduced, which likewise leads to further energy savings. Thus, the azeotrope column can be operated at a significantly lower reflux ratio compared to the known mode of operation.

Likewise, a larger amount of water compared to the known mode of operation is discharged via the top of the predewatering column (7), as a result of which the amount of water obtained in the vessel (14) can be increased. The removal of water via the predewatering column (7) can therefore be operated more effectively. Water is thus removed to a greater degree at an early stage of the process and the load on later process stages for water removal is reduced.

Furthermore, all of the acetic acid is discharged with the bottoms from the azeotrope column (37), so that the feed to the dewatering column (48) and thus also to the pure vinyl acetate column (61) is virtually free of acetic acid. Corrosion phenomena caused by acetic acid in these parts of the plant can therefore be avoided and it is possible to employ a smaller quantity of corrosion-resistant materials. The avoidance of an acetic acid content in the feed to the pure vinyl acetate column (61) also reduces the outlay for the distillation to isolate the pure vinyl acetate, since the removal of residual traces of acetic acid from vinyl acetate is very difficult. The distillation to isolate the pure vinyl acetate can therefore be operated with a lower energy input and at a lower reflux ratio, which generally means a considerable saving of steam.

What we claim is:

1. In a process for separating off vinyl acetate from a gas mixture formed in the reaction of ethylene with acetic acid and oxygen in the gas phase over catalysts comprising palladium or palladium compounds the improvement comprising
    a) introducing the gas mixture leaving the reaction zone into a first distillation column,
    b) cooling the gas mixture leaving the top of the first distillation column to from −20 to +50° C., with the condensate obtained separating into a water phase and an organic phase,
    c) taking off the water phase formed in step b),
    d) recirculating all or part of the organic phase formed in step b) as runback to the top of the first distillation column utilized in step a) and taking off part of the organic phase which is not used as runback,
    e) scrubbing the gas comprising vinyl acetate which is not condensed in step b) in a scrubbing column by means of at least 90% strength aqueous acetic acid and obtaining an acetic-acid solution comprising vinyl acetate at the bottom, f) feeding the bottom product comprising vinyl acetate, ethyl acetate, acetic acid and water from step a) into a collection vessel and depressurizing the pressurized liquid so as to form a gas, g) feeding the liquid obtained in the depressurization in step f) into a second distillation column and taking off a side stream comprising ethyl acetate from an enrichment zone above its bottom, h) utilizing all or part of the bottom product comprising acetic acid and water from step g) for the gas scrub in step e), i) cooling the overhead vapor from step g), with the condensate obtained separating into an aqueous phase and an organic phase, j) taking off the aqueous phase formed in step i), k) recirculating part of the organic phase formed in step i) as runback to the top of the second distillation column utilized in step g) and taking off the remainder, wherein l) part of the bottom product from the scrubbing column utilized in step e) is firstly cooled with pumped circulation and recirculated to the bottom of the scrubbing column utilized in step e), the remainder is taken off and the part taken off is heated to a temperature of at least 30° C. and fed into the lower part of the first distillation column utilized in step a), m) the remaining organic phase taken off in step d) is depressurized, the gas formed in the depressurization is combined with the gas formed in step f) and the combined gas is returned to the process, n) the organic phase obtained in step m) is combined with the organic phase obtained in step i) and the remaining part of the organic phase taken off in step k) which has not been used as runback is introduced into a third distillation column, o) the overhead product from the third distillation column in step n) is cooled and the low boilers obtained and the water obtained are separated off, p) the bottom product from the third distillation column in step n) is introduced into a fourth distillation column, q) pure vinyl acetate is taken off at the top of the fourth distillation column used in step p).

2. The process of claim 1, wherein the bottom product taken off from the scrubbing column is heated to a temperature of from 60° C. to 120° C., in step l).

3. The process of claim 1, wherein the bottom product taken off in step l), is fed into the first distillation column utilized in step a) at the $2^{nd}$ to $15^{th}$ plate, calculated from the bottom of the column.

4. The process of claim 1, wherein the recirculation of the bottom product taken off in step l) to the first distillation column utilized in step a) is carried out in such a way that the outflow from the bottom of the first distillation column has a temperature of from 80° C. to 150° C.

5. The process of claim 1, wherein the bottom product from step a) is depressurized to a pressure of from 0.02 to 0.2 MPa, in the collection vessel in step f).

6. The process of claim 1, wherein a residual organic phase taken off in step d) is fed to a depressurization vessel and depressurized to a pressure of from 0.02 to 0.2 MPa, in step m).

7. The process of claim 1, wherein the cooling temperature in step b) and the proportion of the organic phase formed in step b) which is utilized as runback in step d) are selected so that virtually all the ethyl acetate is present in the bottom product from the first distillation column of step a).

8. The process of claim 1, wherein the part of the organic phase which is not used as runback in step d) is increased, with the organic phases combined in a phase separator in step n) contain very little ethyl acetate.

9. The process of claim 1, wherein in step n) the amount of the combined organic phase which is recirculated as runback is only the amount required for the overhead vapor from the second distillation column to contain very little acetic acid and ethyl acetate.

10. The process of claim 1, wherein the amount of the cooled overhead product returned as runback to the third distillation column in step o) is the amount necessary for a sufficient part of the low boilers and water to be separated off.

11. The process of claim 1, wherein the gas mixture leaving the reaction zone is firstly cooled to from 115° C. to 150° C. by means of the colder circulating gas in the countercurrent heat exchanger and only then introduced into the first distillation column in step a).

12. The process of claim 2, wherein the temperature is 60° to 100° C.

13. The process of claim 3, wherein the plates are the $5^{th}$ to $10^{th}$.

14. The process of claim 5, wherein the pressure is from 0.1 to 0.15 MPa.

15. The process of claim 6, wherein the pressure is 0.1 to 0.15 MPa.

* * * * *